United States Patent [19]

Dooley et al.

[11] Patent Number: 5,059,702

[45] Date of Patent: Oct. 22, 1991

[54] $^{124}$SN-LABELLED TETRA-N-BUTYLTIN AND TRI-N-BUTYLTIN BROMIDE

[75] Inventors: Carol A. Dooley, San Diego, Calif.; John P. Testa, Jr., Oklahoma City, Okla.

[73] Assignee: The United States of America as represented by the Secretary of the Navy, Washington, D.C.

[21] Appl. No.: 414,994

[22] Filed: Sep. 29, 1989

[51] Int. Cl.$^5$ .............................................. C07F 7/22
[52] U.S. Cl. ....................................... 556/104; 556/95
[58] Field of Search .......................... 534/10; 424/1.1; 556/95, 96, 104

[56] References Cited

U.S. PATENT DOCUMENTS

| | | | |
|---|---|---|---|
| 3,248,411 | 4/1966 | Neumann et al. | 556/104 |
| 3,340,283 | 9/1967 | Gloskey | 556/104 |
| 3,389,158 | 6/1968 | Kushlefsky | 556/104 |
| 4,058,545 | 11/1977 | Gitlitz | 260/429.7 |
| 4,087,516 | 5/1978 | Laidler et al. | 424/1 |
| 4,222,950 | 9/1980 | Gitlitz | 260/429.7 |
| 4,511,551 | 4/1985 | Cardarelli et al. | 424/1.1 |
| 4,533,541 | 8/1985 | Srivastava | 424/1.1 |
| 4,826,672 | 5/1989 | Milius et al. | 424/1.1 |

OTHER PUBLICATIONS

*Chem. Pham Bull.* 23: 2944(1975), Drahowzal, F. A. and Wiesinger, F.
*Synth. React. Inorg. Met.-Org. Chem.* 7: 455 (1977), Meinema, H. A. and Martens, H. F.
*J. Labelled Cmpd.* 2: 339 (1966), Otto, P. Ph. H. L., Creemers, H. M. J. C. and Luijten, J. G. A.
*Envon. Res.* 13: 56 (1977), Brown, R. A., Nazario, C. M. de Tirado, R. S., Castrillon, J. and Agard, E. T.
*J. Labelled Cmpd.* 4: 54 (1968), Tenny, K. D. and Tenny, A. M.
*Toxicol. Environ. Health* 5: 871 (1979), Evans, W. H., Cardarelli, N. F. and Smith, D. J.
*J. Agric. Food Chem.* 28: 117 (1980), Kimmel, E. C., Casida, J. E. and Fish, R. H.
*Biochem. J.* 105: 1261 (1967), Bridges, J. W., Davies, D. S. and Williams, R. T.
Aquatic Toxicology and Hazard Assessment: Fourth Conference, ASTM STP 737 (D. R. Branson and K. L. Dickson, Ed.) ASTM pp. 183-200 (1981), Ward, G. S., Cramm, G. C., Parrish, P. R., Trachman, H. and Slesinger, A.
*Environ. Sci. Technol.* 20: 884 (1986), Laughlin, R. B. Jr., French, W. and Guard, H. E.
*Mar. Environ. Res.* 17: 145 (1985), Lee, R. F.
*Proc. Ann. Mar. Coatings Conf.* 18: 10 pages (1978), Sheldon, A. W. and Slesinger, A. E.
*Pestic. Sci.* 11: 77 (1980), Barug, D. and Vonk, J. W.
*Gidrobiol. Zhurn.* 9(6): 59 (1973), Stroganov, N. S., Parina, O. V. and Sorvachev, K. F.
*Tetrahed. Lett.* No. 5291 (1966), Occolitz, J. L.
*Bull. Soc. Chim. Belges* 77: 43 (1968), Boue, S., Gielen, J. and Nasielski, J.
*Chem. Soc. (A)*: 1759 (1967), Chambers, D. B., Glockling, F. and Weston, M.
*J. Organomet. Chem.* 12: 363 (1968), Gielen, M. and Mayence, G.
*Anal. Chem.* 59: 2506 (1987), Clayton, C. A., Hines, J. W. and Elkins, P. D.

*Primary Examiner*—John S. Maples
*Attorney, Agent, or Firm*—Harvey Fendelman; Thomas Glenn Keough

[57] ABSTRACT

Stable isotope-labelled tetra-n-butyl(124)tin was synthesized by the reaction of n-butylmagnesium bromide with $^{124}$SnCl$_4$ and tri-n-butyltin bromide was synthesized by bromine cleavage of the tetraalkyltin. The tri-n-butyl(124)tin compound labelled with the stable isotope $^{124}$Sn is useable in environmental, chemical and biological applications to determine the fate, uptake and metabolism of tributyltin compounds. This determination is made by tracing the chemical, biological and physical processes by using gas chromatography(GC) and electron impact low resolution mass spectrometry(MS). The simplified spectra of the isotopically enriched compounds leads to a twofold increase in detection sensitivity by the GC and MS techniques.

8 Claims, 3 Drawing Sheets

[124]SN-LABELLED TETRA-N-BUTYLTIN AND TRI-N-BUTYLTIN BROMIDE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Tri-n-butyltin compounds are used widely as antifoulant coatings and, as a consequence, have caused increased environmental concern. Their environmental fate is not completely understood and their degradation pathways are uncertain.

Tri-n-butyltin compounds which contain the radioisotopes $^3$H, $^{14}$C and [113]Sn have been synthesized. Tri-n-butyltin oxide, and some related compounds, labelled with $^{14}$C have been used for metabolism and accumulation studies in mammals, in fish, and in marine invertebrates. Studies have looked at complete mineralization of tri-n-butyltin oxide in soil using $^{14}$C-labelled compounds. [113]Sn-labelled tri-n-butyltin oxide was used for metabolic studies in mice and in fish.

Although radioactive isotopes are easy to detect, there are hazards and regulatory complications associated with their use. In addition, in the case of [14]C- and $^3$H-labelled compounds, the detection and localization of radioactivity does not ensure its association with the tin atom.

Thus, there is a continuing need in the state of the art for a means for determining tri-n-butyltin chemical and biological pathways which does not impose a physiological or political hazard associated with their use and which accurately ensures the localization and detection of the compound of interest.

SUMMARY OF THE INVENTION

The present invention is directed to providing a compound tri-n-butyl(124)tin that is synthesized by reaction of bromine with tetra-n-butyl(124)tin that is labeled with the stable isotope [124]Sn to be used in environmental, chemical and biological applications to determine the fate, uptake and metabolism of tributyltin compounds. The compound has the properties to enable such determination by gas chromatography(GC) and mass spectrometry(MS) detection techniques.

An object of the invention is to provide a tracer associated with the tri-n-butyltin compounds used, for example, in antifoulant coatings.

An object of the invention is to provide a stable isotope tracer associated with the tri-n-butyltin compounds used, for example, in antifoulant coatings.

Another object of the invention is to provide a tracer for an antifoulant compound which introduces no additional hazard associated with its use.

Yet another object of the invention is to provide a tracer having the property that products resulting from chemical and biological process are readily identified and distinguished from naturally occurring tin compounds.

Yet another object of the invention is to provide a tracer for tri-n-butyltin that enables a simplified spectra that enhances the sensitivity of detection by GC and/or MS techniques.

A further object of the invention is to provide a tracer for a tri-n-butyltin that affords an increased sensitivity for a selected detection means.

A further object is to provide a tracer for tri-n-butyltin compounds that does not impose a radiation hazard. These and other objects of the invention will become more readily apparent from the ensuing specification with taken in conjunction with the claims and the associated drawings.

DESCRIPTION OF THE PREFERRED EMBODIMENT

Figure 1:
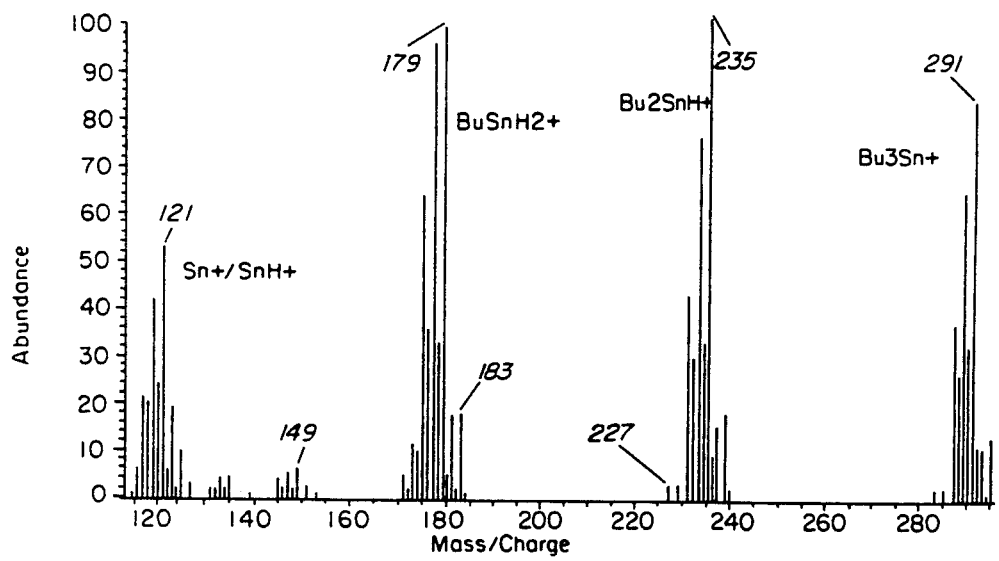
FIG. 1 depicts a mass spectrum of natural tetrabutyltin.

Tri-n-butyl(124)tin bromide and its intermediate tetra-n-butyl(124)tin were synthesized with the compounds enriched to 97.4% in [124]Sn. A low abundance stable isotope at either the heavier or lighter end of the mass range of naturally occurring tin has been found to be most desirable as a tracer. Although [112]Sn is lower in natural abundance than [124]Sn, it is also much more expensive. Largely, for this reason, [124]Sn was selected for the synthesis.

These labelled compounds can be used to trace chemical, biological and physical processes in environmental and metabolic studies. An MS is necessary to identify the compounds of interest. The mass spectra of the synthesized compounds and a derivative of tributyltin bromide demonstrate the utility of mass spectrometric detection and identification of these compounds when used in tracer studies.

The constituents for the labelled compounds were gathered from reliable sources to assure purity and suitability for the intended use. Anhydrous tetrachloro(124)tin was obtained from U.S. Services, Summit, N.J. Florisil, 100/200 mesh, was obtained from Supelco Inc., Bellefonta, Penna. Tetra-n-butyltin (98% purity), 2.0 M n-butylmagnesium bromide in diethylether and 2.0 M n-hexylmagnesium bromide in diethylether were purchased from Aldrich Chemical Company, Milwaukee, Wis. Tri-n-butyltin bromide was purchased from Alfa Products, Danvers, Mass.

The retention times and mass spectra of synthesized and purchased compounds were obtained with a Hewlett-Packard Model 5890A Gas Chromatograph directly connected to a Hewlett-Packard Model 5970 Mass Selective Detector. A Hewlett-Packard 9000-300 Computer using Model 59970C ChemStation software collected the data. Samples were analyzed using splitless injection onto a 12.5 m by 0.1 mm i.d. Hewlett-Packard HP-1 fused silica capillary column with 0.33 um coating thickness. Helium carrier gas was used at a head pressure of 40 kPa. The oven was programmed, after an initial 2 minute hold at 50° C., to 230° C. at 30° C./min. Injector, transfer line and detector were held at 250° C. Masses were scanned between 100 and 450 amu to obtain mass spectra. Detection limits were established using optimal selected ions.

Tetra-n-butyl(124)tin was prepared in accordance with the following procedure. Approximately 1 g anhydrous tetrachloro(124)tin which was enriched in $^{124}$Sn to 97.4% purity was dissolved in 10 ml hexane. The hexane solution was added dropwise to a threefold excess of 2.0 M n-butylmagnesium bromide in diethylether which was cooled to 0° C. in an ice bath. When addition was complete, the reaction mixture was refluxed in a hot water bath for 3 hours. The reaction mixture was again cooled to 0° C. and then hydrolyzed with 3% Hcl. The separated organic layer was shaken with 5% aqueous KF to precipitate contaminating n-butyltin halides as insoluble fluorides. The organic layer was dried with anhydrous $Na_2SO_4$, and the solvent and low boiling impurities were removed by vacuum distillation at room temperature. Purity of the tetra-n-butyl(124)tin product was determined by GC/MS. It was found that yield of the tetra-n-butyltin was approximately 80%.

Preparation of tri-n-butyl(124)tin bromide was as follows. Approximately 1 g tetra-n-butyl(124)tin was suspended in 10 ml reagent grade anhydrous methanol. A stoichiometric amount of bromine dissolved in methanol was added dropwise to the organotin solution at room temperature and in dim light to reduce possible free radical reactions. Upon completion of the bromine addition, the solvent was removed by vacuum distillation. The crude product was cleaned by column chromatography using a 1.5×30 cm Florisil column. The reaction product mixture was eluted first with hexane to remove unreacted tetra-n-butyltin, then with 1:4 (v/v) ethyl acetate/hexane to recover the tri-n-butyltin bromide. Side products with two or more bromine groups remained on the column. The halide was produced in a 80% yield.

Butyltin halides were dissolved in hexane. An excess of 2.0 M hexylmagnesium bromide in diethylether was added and the samples were allowed to react for approximately 20 minutes at 50° C. The samples were hydrolyzed with 1.0 N $H_2SO_4$, and the organic layer was recovered for GC/MS analysis.

Tetraalkyltin compounds exhibit excellent chromatographic characteristics on non-polar columns. Compounds are not lost due to thermal degradation; the compounds are nonpolar, so better peak shape is attained. Simpler spectra, and hence greater sensitivity, are obtained because isotopic contribution from the halides is eliminated. Although trialkytin halides chromatograph fairly well, the mono- and di-substituted alkyltins do not if there is a need to determine their presence. When this is the case, the di-substituted alkyltins require derivatization. Quantification without prior derivatization of alkyltin halides can also be a problem since anion exchange in the hot GC injector can occur.

The tri-n-butyltin bromide spectra are identified. For quantitative analysis, the alkyltin halides routinely are derivatized with an excess of commercially obtained Grignard reagent such as 2.0 M n-hexylmagnesium bromide in diethylether.

Tetraalkyltins exhibit mass spectra characterized by the successive loss of alkyl groups from the tin atom. The parent ion is weak or nonexistent. There is low abundance of tin-containing ions that have lost portions of the original alkyl chain. The most favorable ions are trisubstituted tin; monosubstituted tin atoms are also relatively abundant. Disubstituted tin ions are not very favorable.

For tetra-n-butyltin (Bu=butyl group), prepared from naturally occurring tin, the resulting ion fragments are shown in FIG. 1. Clusters of tin-containing ions center at m/z 121 ($SnH^+$), 179 ($BuSnH_2^+$), 235 ($Bu_2SnH^+$), and 291 ($Bu_3SnH^+$). The clusters are formed by the ten stable tin isotopes, their associated alkyl groups and one or more abstracted hydrogen atoms.

Figure 2:
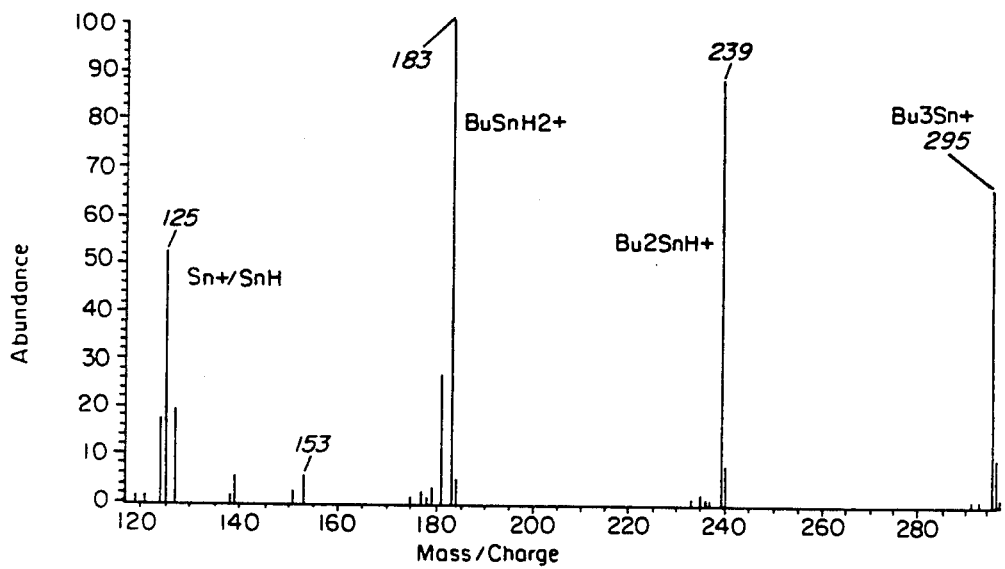
FIG. 2 shows the mass spectrum of tetrabutyl(124)tin.

When naturally occurring tin is replaced with $^{124}$Sn, the mass spectrum is greatly simplified. Major ions occur at m/z 124 ($Sn^+$), 125 ($SnH^+$), 127 ($SnH_3^+$), 181 ($BuSn^+$), 183 ($BuSnH_2^+$), 239 ($Bu_2SnH^+$) and 295 ($Bu_3Sn^+$) in FIG. 2. The low intensity ions at m/z 184, 240 and 296 are $^{13}$C-containing fragments.

Figure 3:
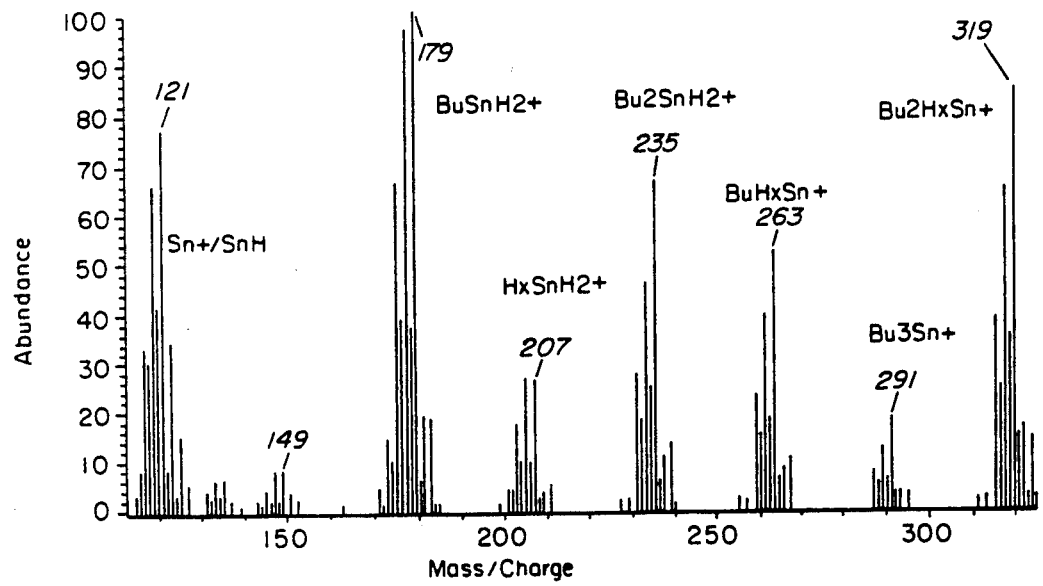
FIG. 3 is the mass spectrum of natural tributylhexyltin.
Figure 4:
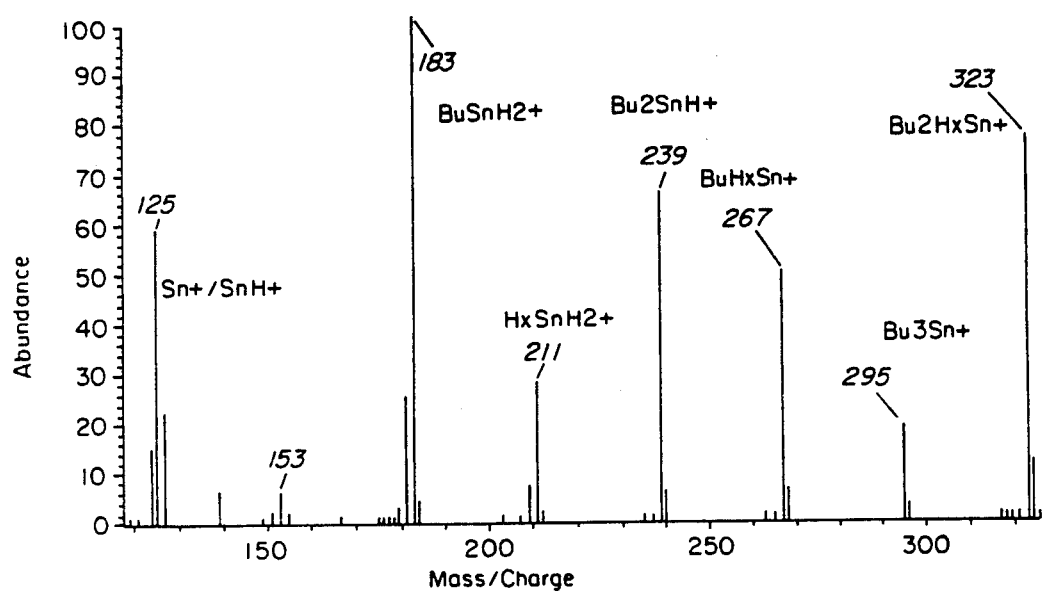
FIG. 4 shows the mass spectrum of tributylhexyl(124)tin.

For tri-n-butyltin-n-hexyltin (Hx=hexyl) prepared from naturally occurring tin, the resulting fragment ions are shown in FIG. 3. The clusters of tin-containing ions center at m/z 121 ($SnH^+$), 179 ($BuSnH_2^+$), 207 ($HxSnH_2^+$), 235 ($Bu_2SnH^+$), 263 ($BuHxSnH^+$), 291 ($Bu_3Sn^+$) and 319 ($Bu_2HxSn^+$). The $^{124}$Sn-containing compound has the simplified spectrum shown in FIG. 4. Major ions occur at m/z 124 ($Sn^+$), 125 ($SnH^+$), 127 ($SnH_3^+$), 181 ($BuSn^+$), 183 ($BuSnH_2^+$), 211 ($HxSnH_2^+$), 239 ($Bu_2SnH^+$), 267 ($BuHxSnH^+$), 295 ($Bu_3Sn^+$) and 323 ($Bu_2HxSn^+$).

Figure 5:
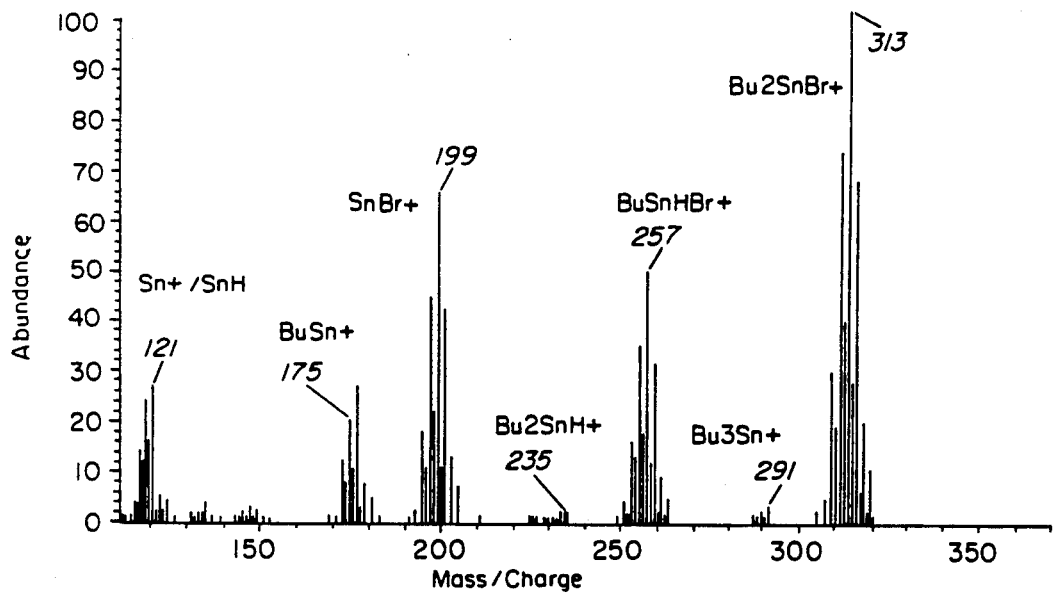
FIG. 5 is the mass spectrum of natural tributyltin bromide.
Figure 6:
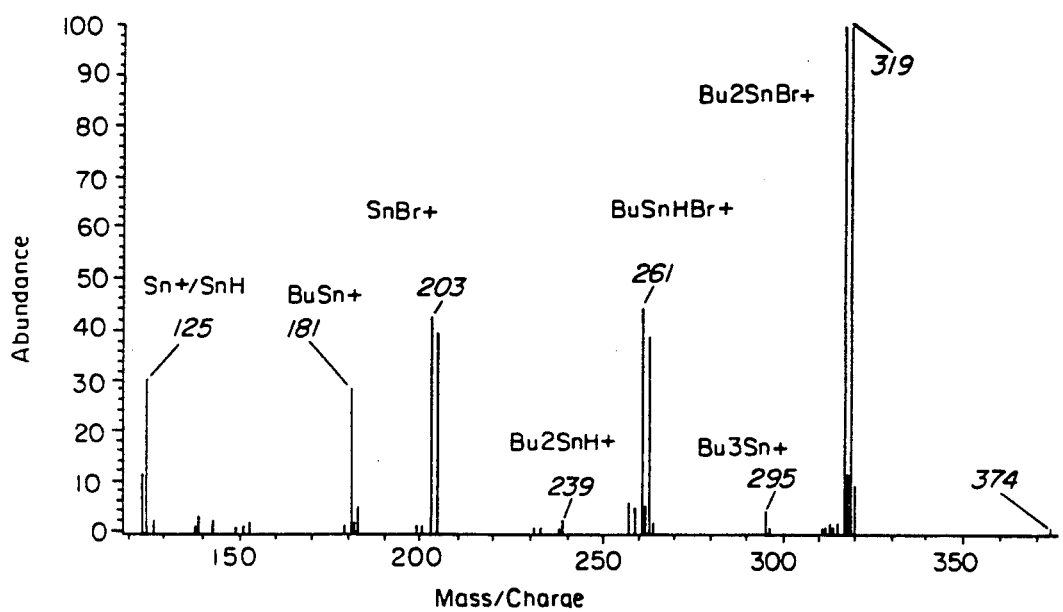
FIG. 6 shows the mass spectrum of tributyl(124)tin bromide.

Trialkyltin halides in general and tri-n-butyltin bromide in particular show a similar pattern of fragmentation to tetraalkyls, in that successive loss of the alkyl groups is favored over halide loss. As shown in FIG. 5, fragment ion clusters occur at m/z 121, 175, 199, 257, and 313 for $SnH^+$, $BuSn^+$, $SnBr^+$, $BuSnHBr^+$, and $Bu_2SnBr^+$, respectively. The largest peak occurring between 100 and 350 m/z is $Bu_2SnBr^+$. The simplified spectrum for $^{124}$Sn, in FIG. 6, shows $SnH^+$ at m/z 125, $BuSn^+$ at m/z 181, $SnBr^+$ at m/z 203 and 205, $BuSnHBr^+$ at m/z 261 and 263, and $Bu_2SnBr^+$ at 317 and 319.

There are several advantages of using $^{124}$Sn compounds as tracers. First, products resulting from chemical and biological processes can be readily identified and distinguished from naturally occurring tin compounds. For this reason, mass balance calculations are simplified and possible redistribution reactions may be resolved. Since these are stable isotopes, there is no additional hazard associated with their use.

The simplified spectra exhibited by these labelled compounds enhances the sensitivity of detection by mass spectrometry. In both full scan and selected ion monitoring, the tin-containing ions reaching the detector are limited to only a few discrete m/z values, rather than being dispersed over the ten stable tin isotopes in each cluster as in the natural compounds. The most abundant natural isotope ($^{120}$Sn) is 32.4% of the total. In the labelled compound the $^{124}$Sn is enriched to 97.4% of the total. Therefore, the theoretical improvement in sensitivity for a single isotope replacing the ten isotope cluster is about a factor of three. However, since several ions are used to insure positive identification of labelled and unlabelled butyltin compounds, the actual increase in sensitivity is only twofold because of computer limitations.

To determine detection limits the method of specified assurance probabilities was used. With the calibration design 1.1 micromolar tri-n-butyltin-n-hexyltin were detected with 95% confidence. With a similar design, 0.4 micromolar tri-n-butyltin-n-hexyltin(124)tin could be detected. With planned refinements in calibration design the detection limit for tri-n-butyltin-n-hexyltin should be reduced to about 0.2 micromolar and that for tri-n-butyltin-n-hexyltin(124)tin to about 0.1 micromolar. Where organotin compounds comprised of naturally occurring tin are present, a five percent spike of labelled organotin must be added to perform a tracer experiment.

Obviously, many modifications and variations of the present invention are possible in light of the above teachings. It is therefore to be understood that within the scope of the appended claims the invention may be practiced otherwise than as specifically claimed.

We claim:

1. A stable-isotope-labelled compound comprising tri-n-butyl(124)tin bromide enriched with the isotope $^{124}Sn$ to produce at least a 5% increase of the amount of the isotope $^{124}Sn$ in the labelled compound over the natural abundance of the isotope $^{124}Sn$ in an unlabelled tin compound.

2. A stable-isotope-labelled organotin compound according to claim 1 in which the enrichment with the stable $^{124}Sn$ isotope is to about 97%.

3. A stable-isotope-labelled organotin compound for tracer studies comprising:
   tetra-n-butyl(124)tin synthesized by the reaction of n-butylmagnesium bromide with $^{124}SnCl_4$ to produce at least a 5% increase of the amount of the isotope $^{124}Sn$ in the labelled compound over the natural abundance of the isotope $^{124}Sn$ in an unlabelled tin compound.

4. A stable-isotope-labelled organotin compound according to claim 3 in which the enrichment with the stable $^{124}Sn$ isotope is to about 97%.

5. A stable-isotope-labelled organotin compound for tracer studies comprising:
   tri-n-butyl(124)tin synthesized by reaction of bromine with tetra-n-butyl(124)tin that has been labelled and enriched with the stable isotope $^{124}Sn$ to produce at least a 5% increase of the amount of the isotope $^{124}Sn$ in the labelled compound over the natural abundance of the isotope $^{124}Sn$ in an unlabelled tin compound.

6. A stable-isotope-labelled organotin compound according to claim 5 in which the enrichment with the stable $^{124}Sn$ isotope is to about 97%.

7. A stable-isotope-labelled organotin compound to determine uptake and metabolism in chemical and biological processes of tributyltin compounds in organisms by gas chromatography(GC) and mass spectrometry(MS) detection techniques comprising:
   tri-n-butyl(124)tin bromide synthesized by reaction of bromine with tetra-n-butyl(124)tin labelled with the stable isotope $^{124}Sn$ to produce at least a 5% increase of the amount of the isotope $^{124}Sn$ in the labelled compound over the natural abundance of the isotope $^{124}Sn$ in an unlabelled tin compound to be used in environmental, chemical and biological applications.

8. A stable-isotope-labelled organotin compound according to claim 7 in which the enrichment with the stable $^{124}Sn$ isotope is to about 97%.

* * * * *